US00PP13429P2

(12) United States Plant Patent
Dolev

(10) Patent No.: US PP13,429 P2
(45) Date of Patent: Dec. 31, 2002

(54) SOLANUM NAMED 'G.U.Y-D ORANGE POM POM'

(75) Inventor: Uri M. Dolev, Santa Barbara, CA (US)

(73) Assignee: Pan Technologies Inc., Santa Paula, CA (US)

( * ) Notice: Subject to any disclaimer, the term of this patent is extended or adjusted under 35 U.S.C. 154(b) by 9 days.

(21) Appl. No.: 09/595,438

(22) Filed: Jun. 15, 2000

(51) Int. Cl.[7] ..... A01H 5/00
(52) U.S. Cl. ..... Plt./263
(58) Field of Search ..... Plt./263, 395

*Primary Examiner*—Bruce R. Campell
*Assistant Examiner*—Anne Marie Grünberg
(74) *Attorney, Agent, or Firm*—Stephen D. Carver

(57) ABSTRACT

A new and distinct variety of a member of the plant family Solanaceae, namely, *Solanum sodomeum*, also known as *Solanum linnaeanum*, and *Solanum hermanii*, commonly known as Apple of Sodom, Yellow Popola, or Dead Sea Apple, named 'G.U.Y.-D Orange Pom Pom', which is characterized by dark green spiny leaves, flowers borne in clusters of three or four, the flowers having white petals and bright yellow stamens, and globose fruits that are reddish-orange.

4 Drawing Sheets

BOTANICAL DESCRIPTION OF THE PLANT

The present invention relates to a new and distinct variety of *Solanum sodomeum*, an erect, diffusely branching woody perennial shrub plant, that is dark green pubescent with stellate and some simple glandular hairs, sparse on upper leaf surface, denser on lower surface. The variety grows to one meter height typically. It features prickles to 15 mm. in length, common on most parts. It spreads by seeds, having flowers, white in color and tomato-like fruits of reddish orange.

The stems, measuring approximately up to 1 meter in height, are greenish in color with curved to straight, straw-colored spines approximately 3–6 mm. long. The central stem is sturdy and erect, and heavily branched with medium foliage. The plant is a moderate to heavy bloomer that does well either outdoors in sunny locations or in green house with bright sunlight.

A young plant of approximately 40 to 86 cm. in height carries 50 to 75 blooms; a more developed plant of approximately 114 cm to 152 cm. in height carries 120 to 160 blooms lasting 5 to 7 days. New blooms appear from 21 to 35 days from transplanting from "plugs" or "seedlings" or 58 to 65 days from seeding.

The leaves typically measure 8 cm.×6 cm. and are dark green in color, ovate, deeply pinnately lobed, spiny, recurved, and petiolate. The leaves are composed of five to seven, rounded to obtuse lobes, the larger ones sinuate. Both stems and leaves are covered with minute star-shaped hairs.

The flowers, similar to those of the potato, have uniformly five to six petals, white in color. Seeds usually fall close to the parent plant but may be dispersed by the wind, in mud, on animals and machinery.

The variety is further characterized by a globose fruit, to 3.8 cm. wide, green marbled, becoming orange to reddish orange, finally brown to black and dry when mature. It contains numerous translucent grayish yellow seeds, round, 2–3 mm. wide.

The flowers have no discernable fragrance.

The seed parent is unknown but is most likely *Solanum*

*sodomeum*. The instant plant is the product of a breeding program and is derived from unknown parents that were raised from solanum seeds found in South America and the Mediterranean. These parents were crossed and the instant plant was chosen from among the progeny because of the white flower and attractive fruit color.

The age of the described plant is 162 days.

The diameter of the central stem at 119 cm. in height is approximately 16.7 mm; the diameter of central stem at 82.6 cm. in height is approximately 8.5 mm.

The bud shape is ovate. The bud size is approximately 7.5 mm to 10 mm in length×3 mm in width.

The petal size is approximately 10 mm to 12 mm in length×5 mm in width.

The depth of foliage lobes is approximately 10 mm to 101 mm.

The seed size is approximately 2–3 mm in diameter.

The plant is resistant to whitefiles and spider mites; and it is resistant to mildew and fungus.

Subsequent to the origination of the variety, I have successfully reporduced it at 19 Canyon Acres, at Santa Barbara, Calif. retaining the distinguishing characteristics through succeeding propagation by cuttings.

The descriptive matter which follows pertains to plants grown and color values observed in those plants in the months of January through April. The plants were grown outdoors in Santa Barbara, Calif. and are believed to be accurate standards for this same cultivar in similar conditions of soil and climate elsewhere.

The observed growth rate is as follows:

From a seed to starter plant: 40 to 45 days.

From a starter plant of approximately 76 mm to 102 mm in height, to mature plant of approximately 109 cm. in height: 185 days. More particularly, the observed growth rate from a starter plant is approximately as follows:

Day 30: 15 cm. to 22.8 cm.

Day 60: 30.5 cm.

Day 90: 63.5 cm.

Day 120: 83.5 cm.

Day 150: 106.7 cm.

Day 185: 109 cm.

The instant variety grows to approximately 120 cm. to 150 cm. in height. In Australia plants of the same genus and species can be bush-like spreading to over 600 cm. in width. While the instant plant has thorns of 3–6 mm in length, others have spikes (thorns) that are longer and more woody or harder. Flower color of other species of Solanum is typically yellow or purple in color, while the instant plant features with white petals. Seeds of other Solanum are 1 mm in diameter and shiny black-brown in color with no seed coat, while the seeds of instant variety are enclosed in a seed coat of somewhat translucent grayish-yellow color measuring approximately 2–3 mm in diameter. The main stems of the instant variety are soft and green, while others are typically brown and woody. Unlike other species of Solanum, the instant plant is not noxious.

The color photographs illustrate the variety.

Referring now specifically to the new and distinct variety of *Solanum sodomeum* named 'G.U.Y.-D Orange Pom Pom,' the following is a detailed description thereof in outline; all major color plate identifications being by reference to The Royal Horticultural Society Colour Chart, except where common terms of color definition are employed. In the description of color, dashes such as "138 A–B" mean that the color falls between the two color designations, as opposed to having both colors present on the same organ, or having both colors present on different organs on the plant.

Type: Hardy, bushy, green house or outdoor, exhibition quality or garden decorative potted plant.

Class: Angiospermae

Variety name: G.U.Y.-D Orange Pom Pom.

Flowers borne: Three to four to a stem.

*Quantity of bloom.*—Moderate both outdoors and green house grown.

*Bud.*—Color is near green white, 157 C.

*Pedicel.*—Stout. Medium to long, averaging 25 to 35 mm; yellow green, 146 C–D with light to occasionally heavy tinting of bronze.

*Hairs.*—Pubescent with stellate and some simple glandular hairs; sparse on upper leaf surface, denser on lower surface.

*Calyx.*—Color is near yellow green, 145 B–C.

*Opening.*—Opens well in climate where temperature does not fall below 10 centigrade.

*Corolla.*—Five or six petals white, between 155B and 155D, in color.

*Size when fully open.*—2.5 cm. to 5 cm. wide.

*Petalage.*—Five or six arranged regularly.

*Form.*—Rotate. The petal lobes remain at first somewhat tightly cupped, becoming at maturity more flattened, spreading and collectively star-shaped in appearance in face view.

*Petals.*—Average thickness or substance with a sheen to the upper surfaces and a matte finish on the under surfaces.

*Shape.*—The petal lobes are acute at the apex.

*Color.*—Newly opened flowers from plants grown outdoors, Santa Barbara, Calif.: Outside petals: Upper surface — White. Under surface: The same as the upper surface. General color effect: Newly opened flowers — rotate with white petals.

*Three days open.*—White petal lobes curve inward.

*Flower longevity.*—4 to 5 days from bud with closed sepals to fully opened flower. Holding at fully open with only slight fading of the petals for an additional 2 to 3 days before flower drops.

1. Leaf surface color of mature leaves: Green Group 137 B to 138 A–B;
2. Upper leaf surface color of immature leaves: Green Group 136 A;
3. Lower leaf surface color of mature leaves: Green Group 137 C;
4. Lower leaf surface color of immature leaves: Green Group 137 B;
5. Seeds: Translucent grayish yellow: Group 161 B;
6. Thorns: Yellow-White Group 158 A (body) to Greyed-Yellow Group 160A at tips;
7. Immature fruit marbling: White Group 155 D, Yellow Green Group 154 C–D, Green Group 138 A–B.
8. Bronze tint on pedicel: Purple Group 79 C–D.
9. Leaf margins: From near greyed purple, 183 C–B, to yellow green, 146 C–D.;
10. Main stems: Yellow-Green Group 146 C–D, 183 C–B;
11. Veins: Yellow-White Group 158 B;
12. Rachis: Yellow-Green Group 146 C–D with 79 C–D;
13. Throat color on blossom: White Group 155 B;
14. Pollen: Yellow Group 11 A to B;
15. Stamen: Yellow Group 12 A;
16. Bud: Yellow White Group 157 C;
17. Calyx: Yellow Green Group 145 B–C.

Reproductive organs:

*Stamens.*—Five, bright yellow, ca. 5 mm long.

*Filaments.*—ca. 1–2 mm long.

*Pollen.*—Abundant.

*Pistil.*—One, 8–11 mm long.

*Style.*—One, 6–9 mm long, stigma greenish.

*Ovary.*—One, globose, ca. 2 mm wide, minutely glandular.

*Seed.*—Many.

Sepals: Yellow green 145 B–C.

Foliage:

*Leaves.*—Ovate, deeply pinnately lobed, spiny, recurved, petiolate, to 15 cm. long and 8 cm. wide. Margin: Sinuate (strongly wavy) Color: Ranging from near greyed purple, 183 C–B, to yellow green, 146 C–D, with occasional bronzing of the margins. The surfaces have a matte finish, the hairs sparse on the upper surface and denser on the under surfaces.

Having thus described my invention, I claim:

1. A new and distinct variety of Apple of Sodom plant named "G.U.Y-D Orange Pom Pom" substantially as illustrated and described, characterized by a woody, perennial shrub of approximately one meter in height which can propagate from cuttings, and has dark green spiny leaves, flowers comprising five to six white petals and bright yellow stamens, with the flowers borne in clusters of three or four, and globose fruits colored reddish-orange having translucent grayish-yellow seeds approximately 2 to 3 mm. in diameter.

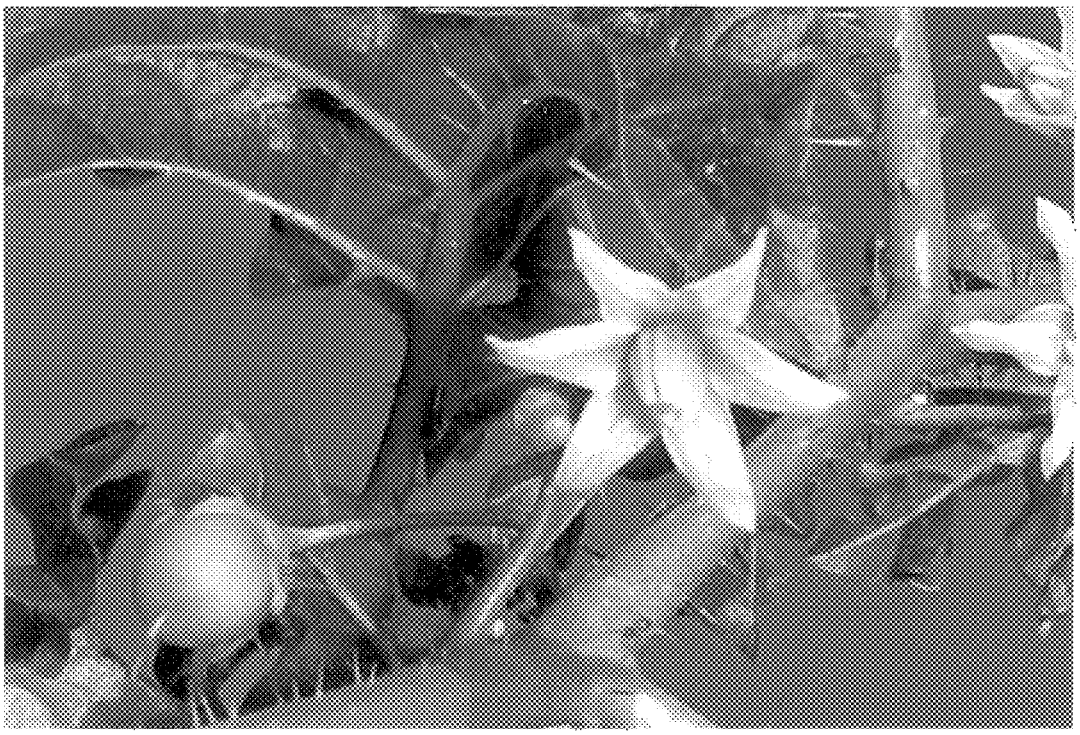
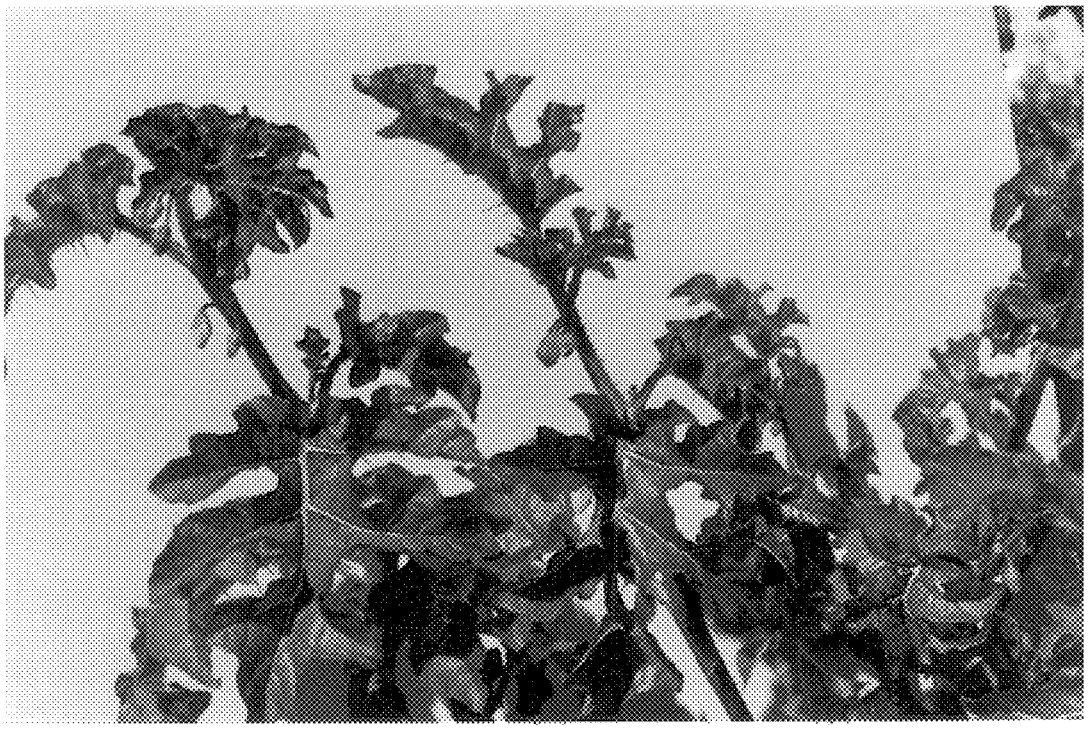

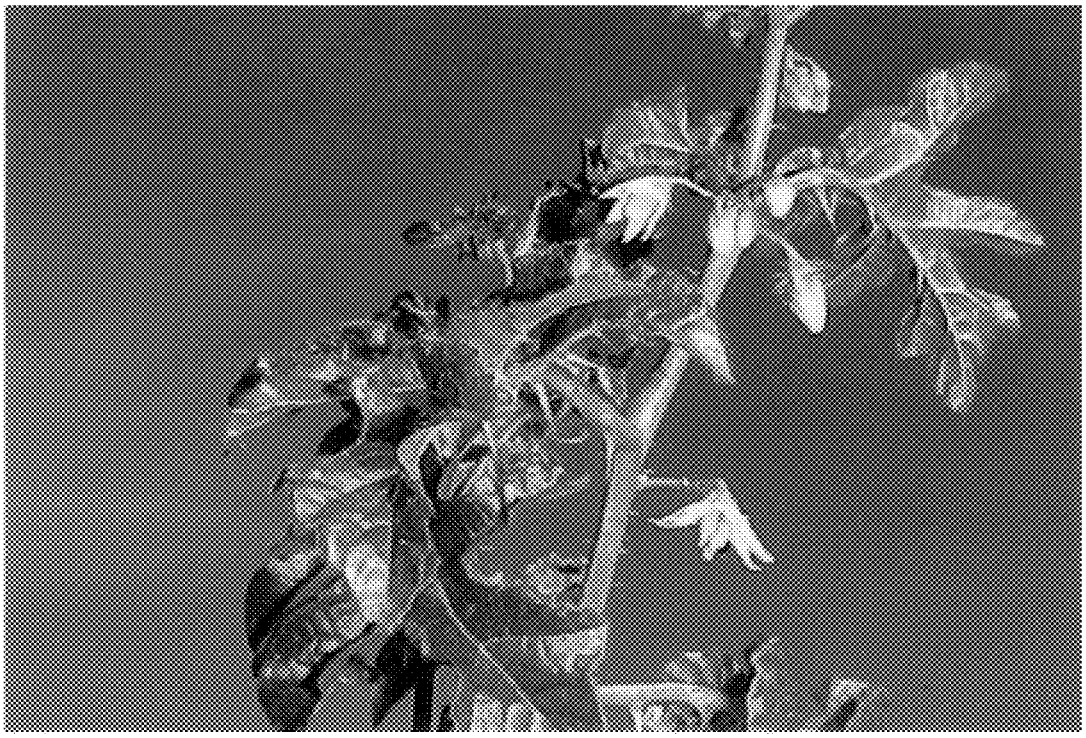
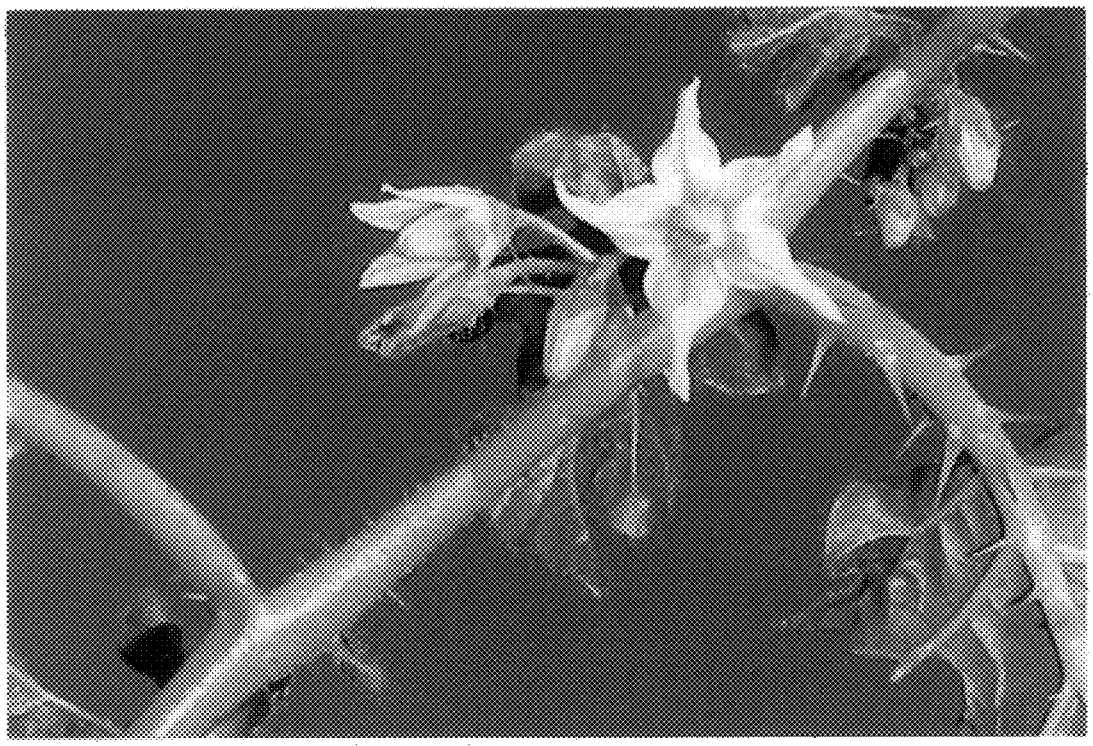

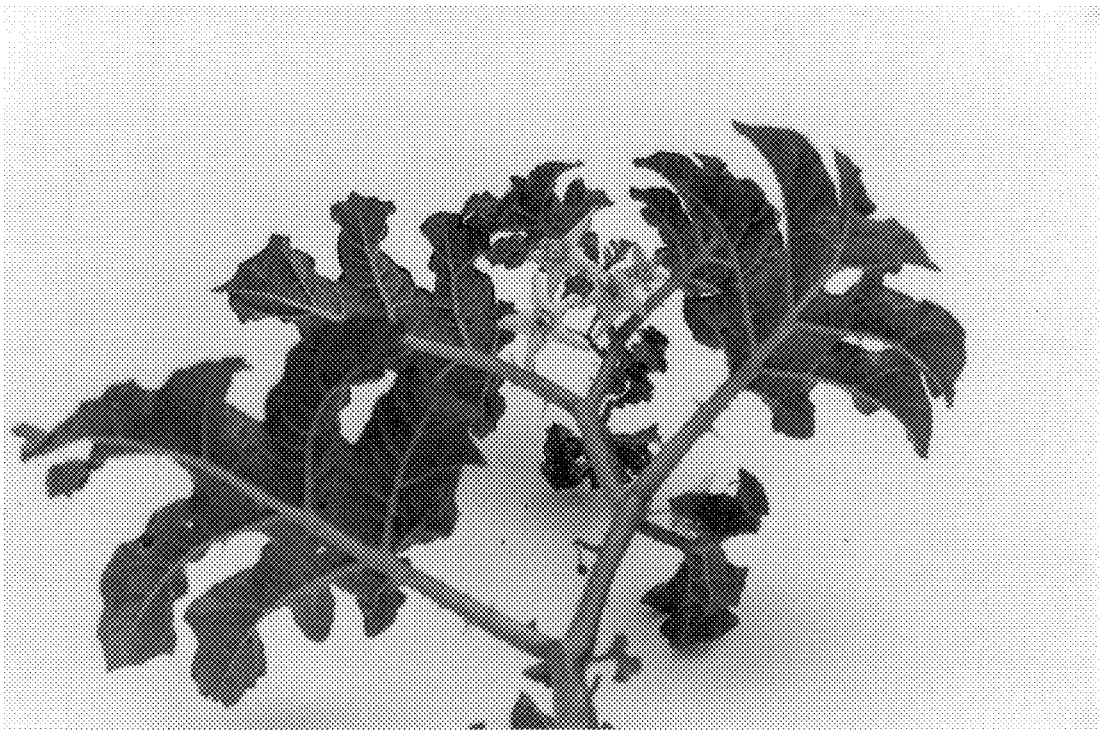
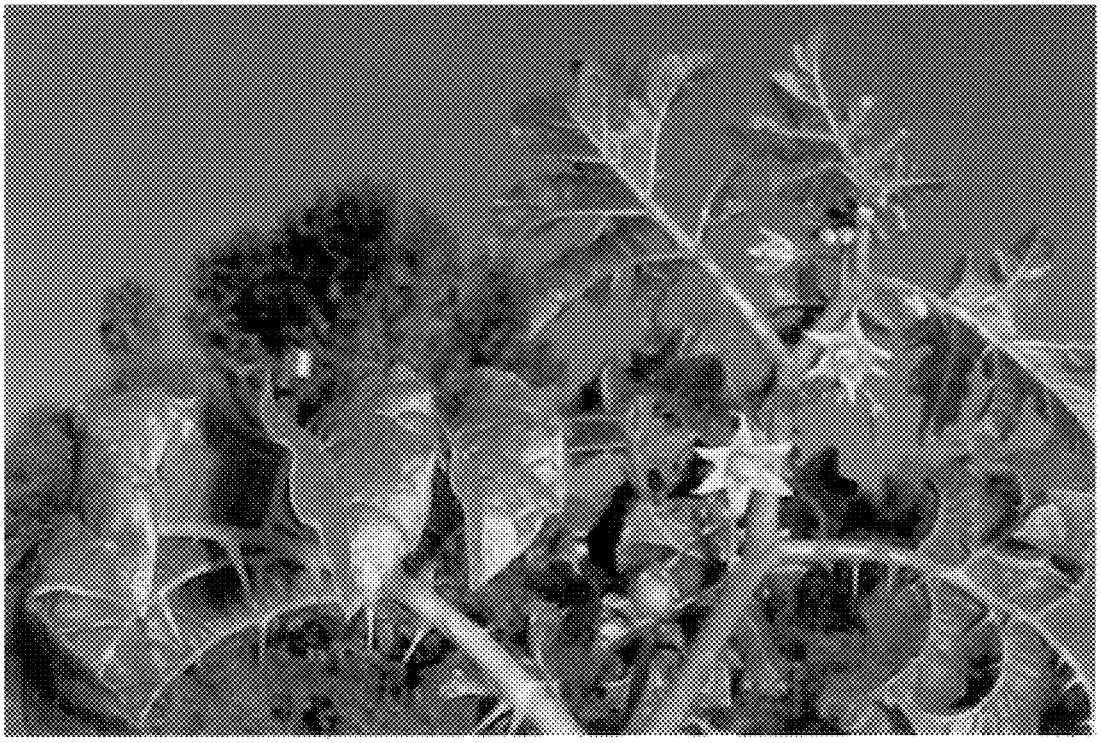

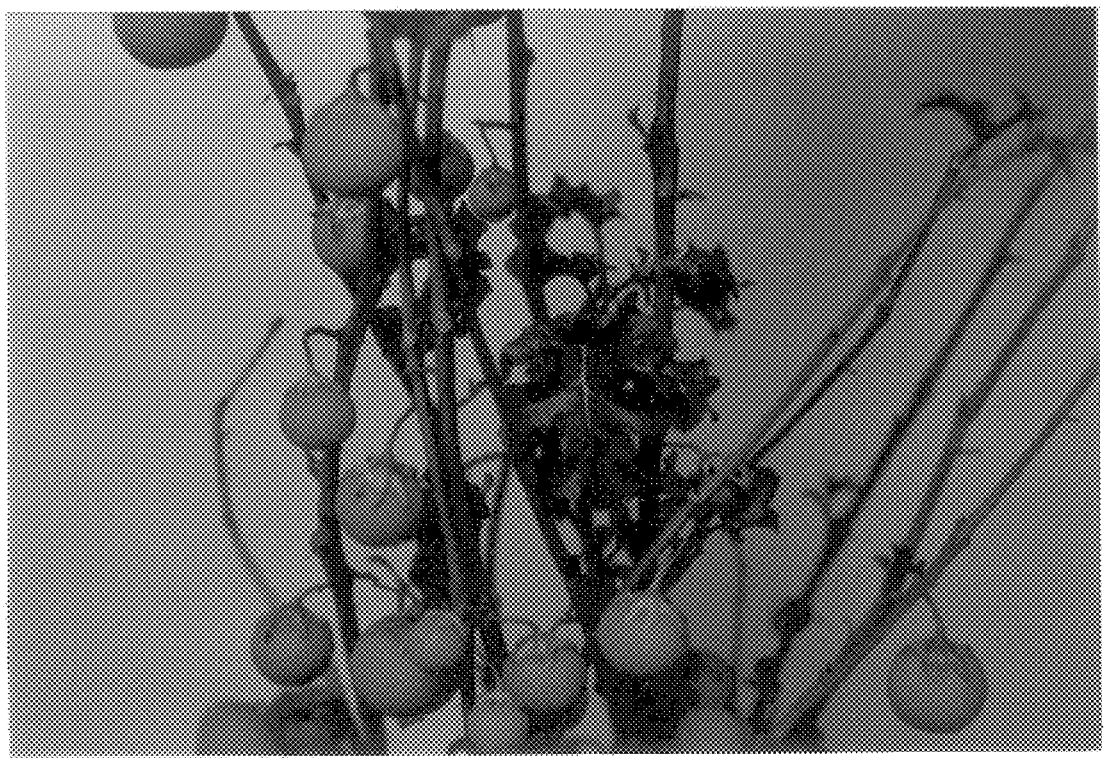
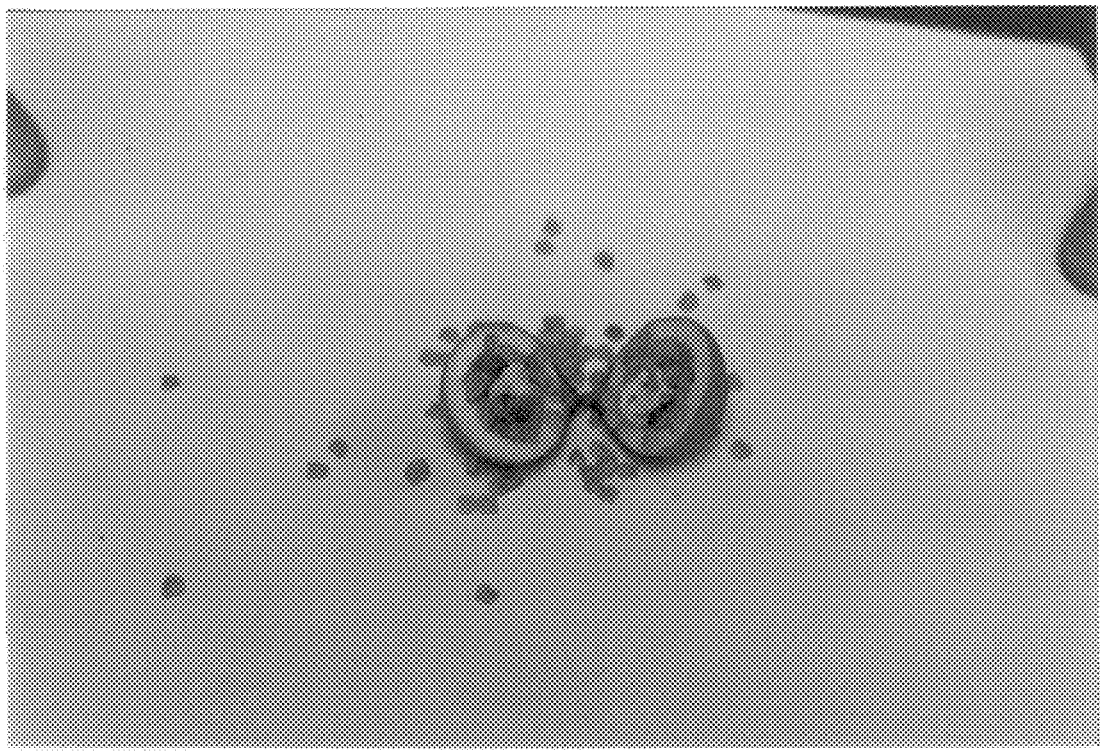

* * * * *